United States Patent [19]

Cramm

[11] Patent Number: 4,609,468

[45] Date of Patent: Sep. 2, 1986

[54] INCREASED STRENGTH POLYMER-BLENDED MEMBRANES

[75] Inventor: Joan A. Cramm, Mount Prospect, Ill.

[73] Assignee: UOP Inc., Des Plaines, Ill.

[21] Appl. No.: 617,053

[22] Filed: Jun. 1, 1984

[51] Int. Cl.$^4$ .............................................. B01D 13/00
[52] U.S. Cl. ...................................... 210/490; 55/16; 210/500.1; 264/185
[58] Field of Search .............................. 264/185, 344; 210/500.2, 490, 491, 654; 55/16, 158

[56] References Cited

U.S. PATENT DOCUMENTS

| | | | |
|---|---|---|---|
| 3,926,798 | 12/1975 | Cadotte | 210/500.2 X |
| 4,071,454 | 1/1978 | Yamamoto et al. | 264/185 X |
| 4,214,994 | 7/1980 | Kitano et al. | 210/490 |
| 4,264,676 | 4/1981 | Uzumaki et al. | 264/344 X |
| 4,406,673 | 9/1983 | Yamada et al. | 55/16 |

*Primary Examiner*—Frank Spear
*Attorney, Agent, or Firm*—Thomas K. McBride; John F. Spears, Jr.; Raymond H. Nelson

[57] ABSTRACT

Polymer blend membranes which possess increased structural strength may be fabricated by preparing a polymer blend membrane comprising a mixture of a phosphoric acid or sulfuric acid and an organic polymer which is at least partially compatible therewith dissolved in a mutually miscible solvent. The resulting polymer blend membrane is then cast upon a porous solid support such as a glass cloth, polysulfone or ceramic and the solvent is allowed to evaporate.

18 Claims, No Drawings

INCREASED STRENGTH POLYMER-BLENDED MEMBRANES

BACKGROUND OF THE INVENTION

Semipermeable membranes may be used for a wide variety of separations involving liquid-liquid separations, liquid-liquid solid separations and gas-gas separations. The membranes which are employed for these purposes usually comprise various organic polymers or mixtures of organic polymers either alone or supported on a porous backing material. For example, semipermeable membranes which are used in desalination processes can comprise cellulose acetate polymers composited on a porous support which acts as a backing for the membrane, thin film composite membranes comprising polymeric compounds such as polyethyleneimine, epiamine, polyethylene, polypropylene films also composited on a porous support such as a polysulfone member, etc. Likewise, gaseous separation membranes may comprise polymeric membranes of cellulose nitrate or cellulose acetate, support membranes having a polymer such as dimethylsilicone, styrene, silicon-carbide copolymers composited thereon, as well as thin film membranes such as polymethylpentene polymers. In addition to these membranes, other permselective membranes such as heteropoly acids may be employed for separating gases such as hydrogen from mixtures of gases in a gaseous stream.

In a majority of cases, the admixture of an organic compound, especially in a polymeric state, with an inorganic compound, results in a phase separation, the two systems being immiscible in nature. However, it has now been discovered that a polymer-blended membrane may be fabricated by admixing a phosphoric acid or sulfuric acid with an organic polymer which is at least compatible with the acid to form a polymer-blended composition of matter, said composition of matter being utilized as one component of a finished membrane which may be used in a gas separation process. The membrane, which is composited on a solid support, possesses unexpected properties which will enable the aforementioned membrane possessing increased strength as well as being highly selective to certain gases to therefore find a use in such separations involving a gas such as hydrogen.

BRIEF SUMMARY OF THE INVENTION

This invention relates to compositions of matter which may be useful as membranes in the separation of various gases. More specifically, the invention is concerned with a membrane in which a thin film inorganic-organic polymer blend is composited on a porous support to provide a composition of matter which may be utilized in gas separation processes.

A conventional operation for separating certain gases from a gas stream containing a mixture of gases whereby a desired gas may be separated and recovered involves the use of membranes which possess a high permeability to the molecular form of the desired gas such as oxygen, hydrogen, nitrogen, etc. These membranes, especially in the case of hydrogen, possess a high permeability to hydrogen whereby molecular hydrogen is transported from the high pressure side of the device, through the membrane and emerges as molecular hydrogen on the low pressure side. Alternatively, separation of gases may be attained by dissociating the desired gas on the high pressure side and transporting it as an ion through the membrane followed by recombining the ions on the low pressure side. Therefore, a desirable membrane for hydrogen separation should possess excellent protonic conductivity properties, membranes which contain both organic and inorganic components will possess this desired property and therefore may be used as hydrogen sensors, hydrogen separation devices, as well as a solid state thin film electrolyte.

It is therefore an object of this invention to provide a novel membrane which may be used in gas separation devices.

A further object of this invention is to provide a method for preparing a two-component membrane comprising a thin film composited on a porous support, the resulting membrane possessing improved structural strength and capable of being utilized for the separation of gases.

In one aspect, an embodiment of this invention may be found in a thin film polymer blend membrane which possesses increased structural strength comprising an organic-inorganic blend of a compound selected from the group consisting of phosphoric acids, sulfuric acid and an organic polymer which is compatible therewith composited on a porous support.

Another embodiment of this invention resides in a method for the preparation of a thin film polymer blend membrane which comprises dissolving a compound selected from the group consisting of phosphoric acids and sulfuric acid and an organic polymer which is compatible therewith in a mutually miscible solvent at solution conditions for a time sufficient to form a blend, casting said blend onto the surface of a porous support, removing said solvent and recovering the resultant thin film polymer blend membrane which possesses increased structural support.

A specific embodiment of this invention resides in a thin film polymer blend membrane which possesses increased structural strength, said membrane comprising a blend of poly(vinyl alcohol) and orthophosphoric acid in which said poly(vinyl alcohol) is present in an amount in the range of from about 99% to about 30% by weight of said blend and said acid is present in an amount in the range of from about 1% to about 70% by weight of said blend, said blend being composited on a glass cloth support.

Another specific embodiment of this invention is found in a method for the preparation of a thin film polymer blend membrane which comprises dissolving poly(vinyl alcohol) and orthophosphoric acid in water at a temperature in the range of from about ambient to about 100° C. for a period of time sufficient to form a blend, casting said blend onto the surface of a glass cloth, removing said water and recovering the resultant thin film polymer blend membrane.

Other objects and embodiments will be found in the following further detailed description of the invention.

DETAILED DESCRIPTION OF THE INVENTION

As hereinbefore set forth, the present invention is concerned with a membrane which may be used in a gas separation process and which will possess increased structural strength, said membrane comprising a thin film inorganic-organic polymer blend composited on a solid porous support. In addition, the invention is also concerned with a method for the preparation of this membrane. As was previously discussed, when attempting to blend an organic polymer with an inorganic-organic compound, the usual result is to obtain a phase separation. However, in contradistinction to this, it has now been discovered that a single phase system may be obtained by mixing certain organic polymeric compounds with a phosphoric acid or a sulfuric acid to form an integral inorganic-organic blend which, when cast upon a suitable surface, will form a thin film semipermeable membrane which, in turn, comprises one component of the finished composite of the present invention. The use of these membranes in gas separation devices is due in some respect to the fact that the membranes will possess a high protonic conductivity, especially at room or ambient temperatures. The membranes which are formed from the blend of the organic polymer and a phosphoric acid or sulfuric acid, when composited on a solid porous support, possess excellent transport properties as well as an increase in tensile strength over those membranes which have been prepared from pure organic polymers. The physical properties which these thin film membranes exhibit thus provide an attractive base for use as gas sensors, especially in the case of hydrogen, or as gas separation membranes. The blend of the organic polymer and the phosphoric acid or sulfuric acid will possess chemical, mechanical and electrical properties which indicate that the two materials form a single phase system. For example, the blends will possess only one glass transition temperature which indicates a single phase system inasmuch as, if the resulting membranes were a two-phase system, or merely a physical mixture, the composition would possess two separate and distinct glass transition temperatures. In addition, the yield strength and modulus of the blend will also be greatly increased over those properties which are possessed by either of the two components. Likewise, another physical characteristic which indicates a single phase or true composition of matter is that the blend is transparent to visible light as well as being uniform in color.

A distinct advantage which is possessed by the polymer blend membranes of the present invention over other organic-inorganic blend membranes lies in the fact that the membranes of the present invention possess low resistivities which are four to five orders of magnitude less than other organic-inorganic polymer blends. Inasmuch as in some electronic devices such as hydrogen sensor devices, it is necessary to measure the output voltage, it will be possible when utilizing a membrane of the instant invention to use a lower impedance voltage measuring device. By using such a device, the cost of the package, that is, everything that is required to measure the concentration of hydrogen, will be lowered and thus will provide a more attractive commercial package due to the less costly and simplified electronic device. In addition, a device with reduced impedance is less sensitive to electromagnetic interference than a high impedance device. This permits the device to be located in an electrically noisy environment without adversely affecting its performance.

One component of the final membrane composition of the present invention, said membrane possessing increased structural strength, comprises a blend of an organic polymer and a phosphoric acid or sulfuric acid, the organic polymer being at least partially compatible with the acid. Examples of organic polymers which may be employed as one component of the blend will include poly(vinyl alcohol), poly(vinyl fluoride), polyethylene oxide, polyethyleneimine, polyacrylic acid, polyethylene glycol, cellulose acetate, polyvinylmethylethyl ether, phenol formaldehyde resins, etc.

The other component of the organic polymer-inorganic blend will comprise a phosphoric acid or sulfuric acid. Examples of phosphoric acids which may be employed will include hypophosphoric acid, metaphosphoric acid, orthophosphoric acid, pyrophosphoric acid, polyphosphoric acid; or aqueous sulfuric acid in which the acid may be present in an amount in the range of from about 10% to 40% of sulfuric acid in the aqueous solution.

It is to be understood that the aforementioned organic polymers, phosphoric acids and sulfuric acid are only representative of the class of compounds which may be employed in formulating the inorganic-organic polymer blend which forms one component of the membrane composition of the present invention, and that this invention is not necessarily limited thereto.

The thin film semipermeable portion of the membrane composite of the present invention may be prepared by admixing the two components of the blend in a mutually miscible solvent at solution conditions for a period of time sufficient to form the desired blend. In the preferred embodiment of the invention the mutually miscible solvent which is employed to dissolve the components comprises water, although it is contemplated within the scope of this invention that any other mutually miscible solvent, either inorganic or organic in nature may also be employed. The mixing of the two components of the composition of matter may be effected at solution conditions which will include a temperature in the range of from about ambient (20°-25° C.) up to the boiling point of the mutually miscible solvent which, for example, in the case of water is 100° C. The time of reaction which is necessary to form the desired blend will vary with the particular organic polymers and phosphoric acids or sulfuric acid as well as the solvent and may be within a period of time ranging from about 0.5 up to about 10 hours or more in duration. In the preferred embodiment of the invention, the polymeric blend of an organic-inorganic compound will possess a molecular weight ranging from about 2000 up to about 135,000 and preferably greater than 10,000. The thickness of the film can be controlled by the amount of phosphoric acid or sulfuric acid and/or the polymer which is present in the reaction mixture. In this respect, it is to be noted that the ratio of phosphoric or sulfuric acid and organic polymer may vary over a relatively wide range. For example, the phosphoric or sulfuric acid may be present in the blend in a range of from about 1% to about 70% by weight of the blend while the organic polymer may be present in an amount in the range of from about 99% to about 30% by weight of the blend. The thin film organic-inorganic blend which is prepared according to the process of the present invention will possess a thickness which may range from about 0.1 to about 50 microns and preferably from about 5 to about 20 microns.

The thin film polymeric membrane may be prepared by placing a predetermined amount of each of the components of the blend, namely the organic polymer and the phosphoric or sulfuric acid in an appropriate apparatus such as a flask. After heating the mutually miscible solvent, the mixture is heated to the desired temperature and allowed to remain, after a thorough admixture thereof, for a predetermined period of time within the range hereinbefore set forth. As an example of the process for preparing the blend, poly(vinyl alcohol) and orthophosphoric acid may be placed in a flask and dissolved in water which has been heated to a temperature of about 90° C.

Upon completion of the desired residence time, the solution is cast upon a porous support. The porous support which is employed to increase the structural strength of the membrane will comprise a compound which possesses a porosity equal to or greater than the porosity of the thin film inorganic-organic blend. It is contemplated within the scope of this invention that any relatively open-celled foam or porous substrate which possesses a structural strength greater than the thin film membrane may be employed. Some examples of these porous supports will include compounds such as glass cloth, polysulfone, cellulose acetate, polyamides, ceramics such as alumina, glass, porcelain, etc. which have been fabricated to possess the necessary porosity, etc. The amount of blend which is cast upon the porous support will be that which is sufficient to form a thin film membrane having a thickness within the range previously set forth. After casting, the mutually miscible solvent such as water is removed by conventional means such as normal evaporation or forced evaporation by the application of external heat, application of vacuum, etc., and the desired membrane comprising the thin film blend composited on the porous support may be recovered and utilized in an appropriate gas separation apparatus or gas sensor apparatus.

Examples of novel thin film inorganic-organic polymer blends composited on a solid support which may be prepared according to the process of this invention will include poly(vinyl alcohol)-orthophosphoric acid composited on a glass cloth, poly(vinyl fluoride)-orthophosphoric acid composited on polysulfone, cellulose acetate-orthophosphoric acid composited on a glass cloth, polyethylene oxide-orthophosphoric acid composited on polysulfone, polyethylene glycol-orthophosphoric acid composited on a glass cloth, poly(vinyl alcohol)-pyrophosphoric acid composited on polysulfone, poly(vinyl fluoride)-pyrophosphoric acid composited on a glass cloth, cellulose acetate-pyrophosphoric acid composited on polysulfone, polyethylene oxide-pyrophosphoric acid composited on a glass cloth, polyethylene glycol-pyrophosphoric acid composited on polysulfone, poly(vinyl alcohol)-metaphosphoric acid composited on a glass cloth, poly(vinyl alcohol)-metaphosphoric acid composited on polysulfone, poly(vinyl fluoride)-metaphosphoric acid composited on a glass cloth, cellulose acetate-metaphosphoric acid composited on polysulfone, polyethylene oxide-metaphosphoric acid composited on a glass cloth, polyethylene glycol-metaphosphoric acid composited on polysulfone, poly(vinyl alcohol)-sulfuric acid composited on a glass cloth, poly(vinyl fluoride)-sulfuric acid composited on polysulfone, cellulose acetate-sulfuric acid composited on a glass cloth, polyethylene oxide-sulfuric acid composited on polysulfone, polyethylene glycol-sulfuric acid composited on a glass cloth, poly(vinyl alcohol)-phosphoric acid composited on alumina, poly(vinyl fluoride)-phosphoric acid composited on porcelain, cellulose acetate-sulfuric acid composited on glass, polyethylene oxide-phosphoric acid composited on alumina, polyethylene glycol-sulfuric acid composited on glass, etc. It is to be understood that the aforementioned list of membrane compositions comprising an inorganic-organic blend composited on a solid porous support is only representative of the class of composites which may be prepared according to the process of this invention and said invention is not necessarily limited thereto.

The increased strength membranes which are prepared according to the process of this invention will possess a relatively greater structural support, thereby enabling the membranes to be produced and handled in a more efficient manner. The aforesaid membranes may be used for either hydrogen sensing or for the separation of gases. The desired device may be prepared by forming the structurally supported membrane and thereafter depositing the conductive metal required for the device on each surface of the membrane. For example, a conductive metal such as platinum, palladium, nickel, copper, etc. may be sputter deposited on the surfaces in such an amount so that the electrode material possesses a thickness ranging from about 100 to about 1000 Angstroms. Following this, the membrane containing the conductive material on both sides thereof may be placed in a desired holder and electrical contact may be made to the electrode and counterelectrode. The sputter deposition which may comprise one method of depositing the conductive material on the membrane may be effected by placing the polymer blended membrane composited on a porous support in a sputter deposition chamber and subjecting the same to the sputter deposition of the conductive metal thereon until the desired thickness of said conductive metal has been attained. In addition, it is also contemplated that the desired conductive metal may be deposited on both surfaces of the membrane composition by any other means known in the art such as impregnation, etc.

The following examples are given for purposes of illustrating the novel membrane composites which possess increased structural strength and to a process for obtaining the same. However, it is to be understood that these examples are merely illustrative in nature and that the membranes and process of this invention are not necessarily limited thereto.

EXAMPLE I

A polymer blend membrane was prepared by dissolving 0.5 gram of 16,000 molecular weight poly(vinyl alcohol) and 0.2 ml of orthophosphoric acid in boiling deionized water, the amount of organic polymer and acid being sufficient to impart a 60/40 wt. % ratio to the resulting polymer blend. After a period of time sufficient to form the blend had passed, the solution was stirred and poured onto the top of a fine glass cloth which was positioned in a standard Petrie dish. The water was allowed to evaporate for a period of 48 hours and the resulting membrane composite comprising a thin film membrane composited on the glass cloth having a thickness of 95 microns was recovered.

EXAMPLE II

In like manner, a polymer blend membrane was prepared by dissolving 0.17 cc of sulfuric acid and 0.5 gram of 16,000 molecular weight poly(vinyl alcohol) in boiling deionized water. After a period of time during which a blend had formed, the solution was poured onto the top of a fine glass cloth positioned in a standard Petrie dish. The water was allowed to evaporate during a period of 48 hours and the resulting membrane composite was recovered.

EXAMPLE III

In a manner similar to that hereinbefore set forth, an inorganic-organic polymer blend may be prepared by dissolving poly(vinyl alcohol) and pyrophosphoric acid in boiling deionized water, the polymer and acid being present in amounts sufficient to impart a 60/40 wt. % ratio to the blend. The solution may then be poured onto the surface of a porous support comprising polysulfone in an amount sufficient so that after evaporation of the water, the polymer blend membrane may possess a thickness of about 50 microns. After evaporation of the water, the membrane composite comprising the polymer blend on the polysulfone may be recovered.

EXAMPLE IV

In this example, a polymer blend membrane may be prepared by dissolving cellulose acetate and potassium phosphate in boiling deionized water and after a time sufficient to form a blend is allowed to elapse, the solution may be poured onto the surface of a glass cloth. After allowing the water to evaporate for a period of 48 hours, the membrane composite may then be recovered.

In like manner, another polymer blend membrane may also be prepared by dissolving poly(vinyl alcohol) having a molecular weight of 16,000 and ammonium phosphate in boiling deionized water. After thorough admixing, the solution may be allowed to stand for a period of time sufficient to form a polymer blend. Following this, the polymer blend may then be poured onto the surface of a porous support comprising polysulfone and after evaporation of the water is allowed to proceed for a period of 48 hours, the resulting composite may be recovered.

EXAMPLE V

To illustrate the gas sensing ability of the composites of the present invention, a sensor was prepared from the polymer blend membrane prepared according to the method as set forth in the above Example I. The sensor was prepared by cutting the supported membrane into a circle having an 11" diameter and platinum electrodes ½" in diameter were sputter dispersed on each side of the membrane. The membrane was then placed in a circular Teflon cell, said sensor being positioned in the middle of said cell to render the two sides of said cell air-tight. A reference gas consisting of 100% hydrogen and a working gas comprising 91.013% nitrogen and 9.987% hydrogen were placed on each side of the cell. The gases were continuously flushed through the cell, the sensor giving off a voltage ranging from 0 millivolts when hydrogen was present on both sides of the sensor to 29.6 millivolts when the reference gas and working gas were present. The latter voltage compares to a calculated voltage of 29.6 millivolts at a temperature of 25.3° C. In addition, it was found that the resistivity was $0.375 \times 10^5$ ohms. In addition, a membrane prepared according to the method set forth in Example II above was tested in like manner and the sensor was found to give off a voltage similar to the membrane comprising a blend of poly(vinyl alcohol) and orthophosphoric acid, the resistivity being somewhat higher.

EXAMPLE VI

As an illustration of the greater structural strength of the polymer blend composited on a porous solid support as exemplified by the blends of the present invention when compared to unsupported membranes, two polymer blend membranes were prepared. The polymer blend was prepared by dissolving 0.5 gram of poly(vinyl alcohol) having a molecular weight of 16,000 and 0.2 ml of orthophosphoric acid in boiling deionized water. The resulting blend was cast onto a glass cloth having a thickness of 30 microns. A second blend was prepared by admixing like proportions of poly(vinyl alcohol) and orthophosphoric acid and casting the resulting blend onto a Petrie dish without a support. After removal of the solvent, the two membranes were recovered.

A burst testing apparatus was prepared by placing the membrane composited on a metal blend having a 1" square hole in the center thereof, said membrane being held in place by a gasket and a metal plate provided with an orifice for the introduction of a gas. Air was forced through the membrane at various pressures for a predetermined period of time to determine the amount of pressure necessary to burst the membrane. The membrane which was supported on a glass cloth was labeled "A" and the unsupported membrane was labeled "B". The results of the burst test are set forth in Table 1 below:

TABLE 1

| A | B |
|---|---|
| 10 lbs/1 min. | 5 lbs less than 1 min. - center |
| 15 lbs/1 min. | expanded until it burst in |
| 20 lbs/1 min. | center. |
| 25 lbs/1 min. | |
| 30 lbs/1 min. | |
| 35 lbs/1 min. Burst shearing at the edges of the hole | |

In addition, another sample of unsupported membrane was placed in the holder and 2 lbs./sq. in. of air was passed over the film. The film expanded into the hole for a distance of about 9 millimeters and held. When the pressure of the air was discontinued, the membrane was removed and it was found that a permanent deformation of the membrane had taken place.

It is readily apparent from the results set forth in the above Table that the polymer blend membrane which was cast on a porous support possessed a greater structural strength than did the unsupported membrane.

I claim as my invention:

1. A supported thin film polymer blend membrane which possesses increased structural strength comprising a porous support having composited thereon an inorganic-organic blend formed as a solution phase blend in a mutually miscible solvent consisting of a phosphoric or sulfuric acid and an organic polymer selected from the group consisting of polyvinyl alcohol, polyvinyl fluoride, polyethylene oxide, polyethylene glycol, and cellulose acetate.

2. The supported thin film polymer blend membrane as set forth in claim 1 in which said acid is present in said blend in an amount in the range of from about 1% to about 70% by weight of said blend.

3. The supported thin film polymer blend membrane as set forth in claim 1 in which said organic polymer is present in said blend in an amount in the range of from about 99% to about 30% by weight of said blend.

4. The supported thin film polymer blend membrane as set forth in claim 1 in which said blend possesses a thickness in the range of from about 0.1 to about 50 microns.

5. The supported thin film polymer blend membrane as set forth in claim 1 in which said acid comprises orthophosphoric acid and said polymer comprises poly(vinyl alcohol).

6. The supported thin fim polymer blend membrane as set forth in claim 1 in which said acid comprises pyrophosphoric acid and said polymer comprises poly(vinyl alcohol).

7. The supported thin film polymer blend membrane as set forth in claim 1 in which said acid comprises orthophosphoric acid and said polymer comprises cellulose acetate.

8. The supported thin film polymer blend membrane as set forth in claim 1 in which said acid comprises sulfuric acid and said polymer comprises poly(vinyl alcohol).

9. The supported thin film polymer blend membrane as set forth in claim 1 in which said porous support comprises glass cloth.

10. The supported thin film polymer blend membrane as set forth in claim 1 in which said porous support comprises polysulfone.

11. A method for the preparation of a thin film polymer blend membrane which comprises dissolving a phosphoric or sulfuric acid and an organic polymer in a mutually miscible solvent at solution conditions for a time sufficient to form a blend consisting of said acid and said organic polymer, casting said blend onto the surface of a porous support, removing said solvent and recovering the resultant thin film polymer blend membrane which possesses increased structural support, said organic polymer selected from the group consisting of polyvinyl alcohol, polyvinyl fluoride, polyethylene oxide, polyethylene glycol, and cellulose acetate.

12. The method as set forth in claim 11 in which said solution conditions include a temperature in the range of from about ambient to about 100° C.

13. The method as set forth in claim 11 in which said mutually miscible solvent comprises water.

14. The method as set forth in claim 13 in which the removal of said water is effected by evaporation.

15. The method as set forth in claim 11 in which said phosphoric acid comprises orthophosphoric acid and said polymer comprises poly(vinyl alcohol).

16. The method as set forth in claim 11 in which said acid comprises pyrophosphoric acid and said polymer comprises poly(vinyl alcohol).

17. The method as set forth in claim 11 in which said porous support comprises glass cloth.

18. The method as set forth in claim 11 in which said porous support comprises polysulfone.

* * * * *